(12) United States Patent
Metcalfe et al.

(10) Patent No.: US 11,819,415 B2
(45) Date of Patent: Nov. 21, 2023

(54) ORTHOPAEDIC IMPLANT SYSTEMS INCLUDING INTERNAL NETWORKS AND METHODS OF REPAIR

(71) Applicant: Arthrex, Inc., Naples, FL (US)

(72) Inventors: Nick Metcalfe, Bonita Springs, FL (US); Reinhold Schmieding, Naples, FL (US); Michael Moreland, Fort Myers, FL (US); Steven Jim DeLeon, Naples, FL (US); David Knopf, Bonita Springs, FL (US); Scott William Doody, Bonita Springs, FL (US); Siddhant Thakur, Naples, FL (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 17/221,049

(22) Filed: Apr. 2, 2021

(65) Prior Publication Data

US 2022/0313440 A1 Oct. 6, 2022

(51) Int. Cl.
*A61F 2/30* (2006.01)
*A61F 2/40* (2006.01)
*A61B 17/80* (2006.01)
*A61B 17/86* (2006.01)

(52) U.S. Cl.
CPC ........ *A61F 2/30734* (2013.01); *A61F 2/4081* (2013.01); *A61F 2002/30736* (2013.01); *A61F 2002/30769* (2013.01)

(58) Field of Classification Search
None
See application file for complete search history.

(56) References Cited

U.S. PATENT DOCUMENTS

| | | | |
|---|---|---|---|
| 5,116,377 A | 5/1992 | Skripitz et al. | |
| 6,455,311 B1 | 9/2002 | Vacanti | |
| 6,740,120 B1* | 5/2004 | Grimes | A61F 2/3601 623/908 |
| 7,488,320 B2* | 2/2009 | Middleton | A61B 17/746 606/92 |
| 7,819,925 B2 | 10/2010 | King et al. | |
| 8,147,558 B2 | 4/2012 | Lee et al. | |
| 8,292,967 B2* | 10/2012 | Brown | A61F 2/30907 623/23.19 |

(Continued)

FOREIGN PATENT DOCUMENTS

| | | |
|---|---|---|
| EP | 2724691 | 6/2015 |
| EP | 3498227 | 6/2019 |

(Continued)

OTHER PUBLICATIONS

Musculoskeletal Key. Arthrex Univers Revers (TM) shoulder prosthesis. Retrieve from: https://musculoskeletalkey.com/arthrex-univers-revers-shoulder-prosthesis/.

(Continued)

*Primary Examiner* — Ann Schillinger
(74) *Attorney, Agent, or Firm* — Carlson, Gaskey & Olds, P.C.

(57) ABSTRACT

This disclosure relates to orthopaedic implant systems and methods for repairing bone defects and restoring functionality to a joint. The implant systems and methods disclosed herein may include augments extending from respective baseplates. The augments may have an internal network for communicating material in the respective implant.

15 Claims, 9 Drawing Sheets

(56) References Cited

U.S. PATENT DOCUMENTS

| | | | |
|---|---|---|---|
| 8,303,665 B2 | 11/2012 | Tornier et al. | |
| 8,632,597 B2 | 1/2014 | Lappin | |
| 8,764,836 B2 | 7/2014 | DeWilde et al. | |
| 8,852,283 B2 | 10/2014 | Tornier et al. | |
| 8,870,962 B2 | 10/2014 | Roche et al. | |
| 8,940,054 B2 | 1/2015 | Wiley et al. | |
| 9,005,184 B2 | 4/2015 | Mayer et al. | |
| 9,066,806 B2 | 6/2015 | Phipps | |
| 9,095,438 B1* | 8/2015 | Wait | A61F 2/3601 |
| 9,114,017 B2 | 8/2015 | Lappin | |
| 9,226,830 B2 | 1/2016 | De Wilde et al. | |
| 9,233,003 B2 | 1/2016 | Rouche et al. | |
| 9,283,083 B2 | 3/2016 | Winslow et al. | |
| 9,351,843 B2* | 5/2016 | Viscogliosi | A61F 2/389 |
| 9,452,055 B2 | 9/2016 | Lappin | |
| 9,532,880 B2 | 1/2017 | Lappin | |
| 9,545,311 B2 | 1/2017 | Courtney, Jr. et al. | |
| 9,545,312 B2 | 1/2017 | Tornier et al. | |
| 9,629,725 B2 | 4/2017 | Gargac et al. | |
| 9,844,440 B2 | 12/2017 | Kovacs et al. | |
| 9,980,819 B2 | 5/2018 | Gray | |
| 10,010,609 B2 | 7/2018 | D'Agostino et al. | |
| 10,034,757 B2 | 7/2018 | Kovacs et al. | |
| 10,251,755 B2* | 4/2019 | Boileau | A61B 17/1635 |
| 10,258,478 B2 | 4/2019 | Kovacs et al. | |
| 10,265,184 B2 | 4/2019 | Lappin | |
| 10,357,373 B2 | 7/2019 | Gargac et al. | |
| 10,383,735 B2 | 8/2019 | Wiley et al. | |
| 10,517,736 B2 | 12/2019 | Lappin et al. | |
| 10,555,816 B1 | 2/2020 | Pappou | |
| 10,688,223 B2 | 6/2020 | Cui et al. | |
| 10,709,814 B2 | 7/2020 | Vickers et al. | |
| 10,722,374 B2 | 7/2020 | Hodorek et al. | |
| 2003/0060889 A1* | 3/2003 | Tarabishy | A61B 17/1617 623/22.17 |
| 2003/0065397 A1* | 4/2003 | Hanssen | A61F 2/30 623/23.23 |
| 2003/0187513 A1* | 10/2003 | Durniak | A61B 17/8802 623/23.62 |
| 2004/0220674 A1 | 11/2004 | Pria | |
| 2004/0225360 A1* | 11/2004 | Malone | A61F 2/446 623/17.11 |
| 2005/0261775 A1 | 11/2005 | Baum et al. | |
| 2005/0278030 A1 | 12/2005 | Tornier et al. | |
| 2006/0015188 A1 | 1/2006 | Grimes | |
| 2006/0200248 A1* | 9/2006 | Beguin | A61F 2/4081 623/19.11 |
| 2008/0119945 A1* | 5/2008 | Frigg | A61B 17/686 606/300 |
| 2010/0042213 A1* | 2/2010 | Nebosky | A61B 17/60 606/280 |
| 2011/0060373 A1* | 3/2011 | Russell | A61B 17/8875 606/86 R |
| 2012/0209392 A1* | 8/2012 | Angibaud | A61F 2/4081 623/19.11 |
| 2012/0261546 A1* | 10/2012 | Hawkins | A61F 2/36 249/160 |
| 2013/0123928 A1* | 5/2013 | Mayer | A61F 2/30721 623/18.11 |
| 2013/0211539 A1* | 8/2013 | McDaniel | A61F 2/28 623/23.53 |
| 2014/0025173 A1 | 1/2014 | Cardon et al. | |
| 2015/0250598 A1* | 9/2015 | Yakimicki | A61F 2/3859 623/23.12 |
| 2016/0317704 A9 | 11/2016 | Lyngstadaas et al. | |
| 2017/0095336 A1 | 4/2017 | Tornier et al. | |
| 2017/0216491 A1 | 8/2017 | Schlachter et al. | |
| 2017/0273801 A1* | 9/2017 | Hodorek | A61F 2/4081 |
| 2018/0021140 A1 | 1/2018 | Angelini et al. | |
| 2018/0140427 A1* | 5/2018 | Conway | A61B 17/8066 |
| 2018/0303618 A1 | 10/2018 | Kovacs et al. | |
| 2018/0333268 A1 | 11/2018 | Cardon et al. | |
| 2019/0015116 A1 | 1/2019 | Gargac et al. | |
| 2019/0015117 A1 | 1/2019 | Neichel et al. | |
| 2019/0015118 A1 | 1/2019 | Neichel et al. | |
| 2019/0015221 A1 | 1/2019 | Neichel et al. | |
| 2019/0151106 A1 | 5/2019 | Kovacs et al. | |
| 2019/0159907 A1 | 5/2019 | Roche et al. | |
| 2019/0240035 A1 | 8/2019 | Lappin | |
| 2019/0298537 A1 | 10/2019 | Gargac et al. | |
| 2019/0358045 A1 | 11/2019 | Boileau et al. | |
| 2020/0030108 A1 | 1/2020 | Orphanos et al. | |
| 2020/0113632 A1 | 4/2020 | Varadarajan et al. | |
| 2020/0155322 A1 | 5/2020 | Walker et al. | |
| 2020/0179126 A1 | 6/2020 | Courtney, Jr. et al. | |
| 2020/0188121 A1 | 6/2020 | Boux de Casson et al. | |
| 2020/0229931 A1 | 7/2020 | Tornier et al. | |
| 2021/0307919 A1* | 10/2021 | Paterson | A61F 2/30771 |
| 2021/0369465 A1* | 12/2021 | Simoes | A61F 2/30942 |
| 2022/0047392 A1* | 2/2022 | de Beaubien | A61F 2/4059 |
| 2022/0183851 A1* | 6/2022 | Deransart | A61F 2/30749 |

FOREIGN PATENT DOCUMENTS

| | | | |
|---|---|---|---|
| EP | 3763335 | 1/2021 | |
| JP | 5955818 | 6/2016 | |
| WO | 2017165346 | 9/2017 | |
| WO | 2018052965 | 3/2018 | |
| WO | 2018081073 | 5/2018 | |
| WO | WO-2018081073 A1 * | 5/2018 | A61B 17/56 |
| WO | 2018136393 | 7/2018 | |
| WO | WO-2020168269 A1 * | 8/2020 | A61B 17/68 |

OTHER PUBLICATIONS

Equinoxe Platform System. Exactech. Retrieved from: https://www.exac.com/extremities/equinoxe-platform-system/.

Equionxe strength in numbers. Exactech. Retrieved from: https://www.exac.com/wp-content/uploads/2021/06/12-0000039_Equinoxe_Main_Brochure_Web.pdf.

International Search Report for International Application No. PCT/US2022/020681 dated Jun. 28, 2022.

* cited by examiner

ORTHOPAEDIC IMPLANT SYSTEMS INCLUDING INTERNAL NETWORKS AND METHODS OF REPAIR

BACKGROUND

This disclosure relates to orthopaedic procedures and, more particularly, to orthopaedic implant systems and methods for repairing bone defects and restoring functionality to a joint.

Many bones of the human musculoskeletal system include articular surfaces. The articular surfaces articulate relative to other bones to facilitate different types and degrees of joint movement. The articular surfaces can erode or experience bone loss over time due to repeated use or wear or can fracture as a result of a traumatic impact. These types of bone defects can cause joint instability and pain.

Bone deficiencies may occur along the articular surfaces. Some techniques utilize a bone graft and/or implant to repair a defect adjacent the articular surfaces. The implant may be secured to the bone utilizing one or more fasteners.

SUMMARY

This disclosure relates to orthopaedic implant systems and methods. The implant systems may be used during methods for repairing bone defects. The implant systems described herein may be utilized to restore functionality to a joint and include implants having an internal network for communicating various materials in the respective implant.

An orthopaedic implant system of the present disclosure may include an implant including a baseplate and an augment. The baseplate may include a plate body extending between front and rear faces. The front face may be configured to face towards an opposed articular surface associated with a bone. The augment may include an augment body extending from the rear face of the plate body. The augment body may include a network of internal passages that branch to respective ports along an external surface of the augment body.

An orthopaedic implant system of the present disclosure may include an implant including a baseplate and an augment extending from the baseplate. A front face of the baseplate may be configured to face towards an opposed an articular surface associated with a bone. The augment may include an augment body including a network of internal passages coupled to respective ports along an external surface of the augment body. A pump may be configured to communicate biological material at least partially into the network.

A method of installing an orthopaedic implant of the present disclosure may include positioning an implant along a surgical site. The implant may include a baseplate and an augment. The baseplate may include a plate body extending between front and rear faces. The augment may include an augment body extending from the plate body. The augment body may include a network of internal passages coupled to respective ports along an external surface of the augment body. The positioning step may occur such that the front face of the baseplate faces towards an opposed articular surface associated with an adjacent bone.

The various features and advantages of this disclosure will become apparent to those skilled in the art from the following detailed description. The drawings that accompany the detailed description can be briefly described as follows.

BRIEF DESCRIPTION OF THE DRAWINGS

Like reference numbers and designations in the various drawings indicate like elements.

DETAILED DESCRIPTION

Figure 1:
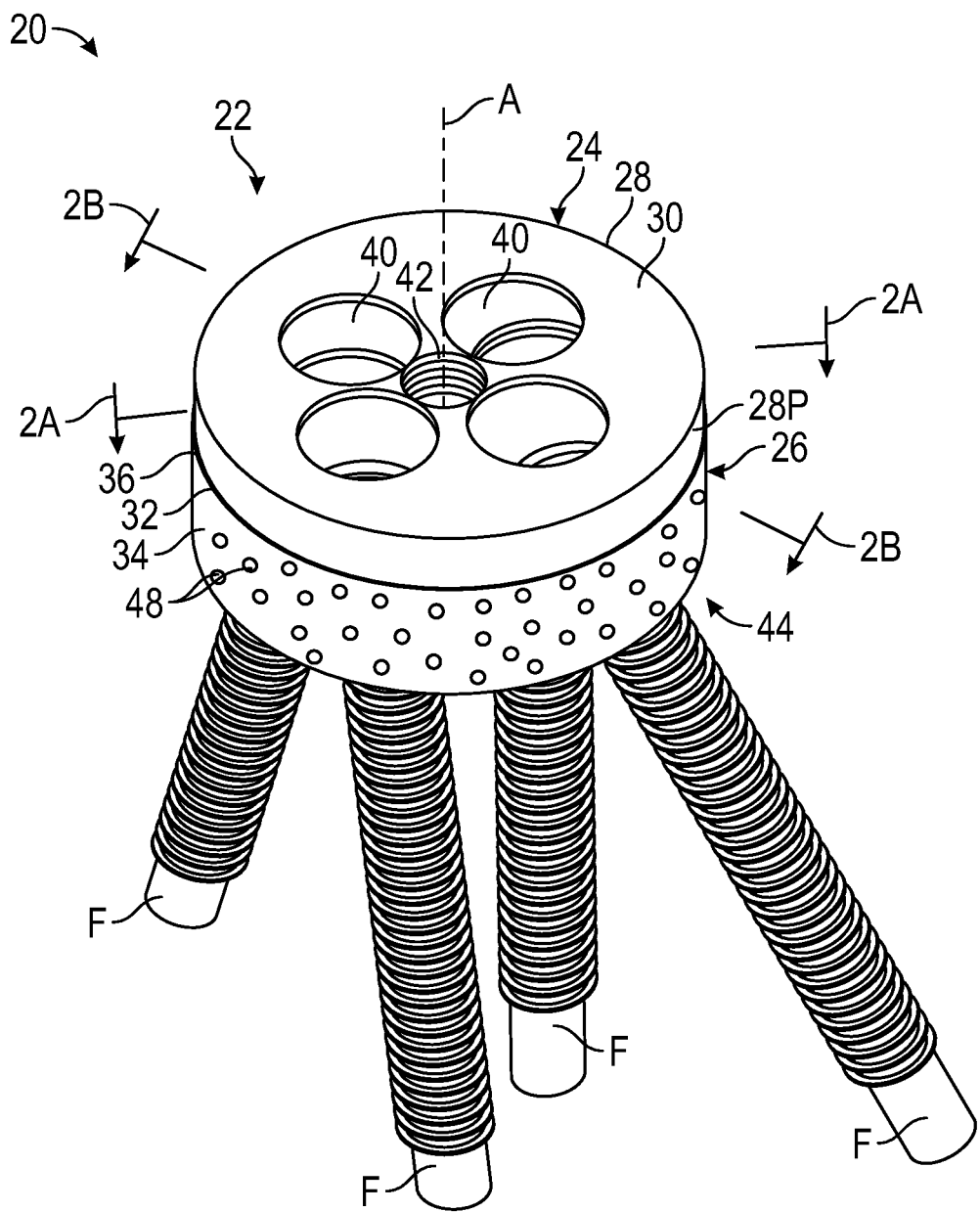
FIG. 1 illustrates a perspective view of an exemplary orthopaedic implant of an implant system including a baseplate and augment.

This disclosure relates to orthopaedic implant systems and methods for repairing bone defects. The implant systems described herein may be utilized during arthroplasty procedures and may include implants incorporated into a prosthesis for restoring functionality to shoulders and other joints having advanced cartilage disease. The implants may include an augment that extends from a respective baseplate. The implants may be situated along a surgical site such as the glenoid face to at least partially fill a bone void. The augment may include an internal network for communicating biological and/or other material in the respective implant, which may improve fixation and healing of the patient.

An orthopaedic implant system according to an exemplary aspect of the present disclosure may include an implant including a baseplate and an augment. The baseplate may include a plate body extending between front and rear faces. The front face may be configured to face towards an opposed articular surface associated with a bone. The augment may include an augment body extending from the rear face of the plate body. The augment body may include a network of internal passages that branch to respective ports along an external surface of the augment body.

In some embodiments, the network may be dimensioned to branch outwardly from the rear face of the plate body to opposed sidewalls of the augment body.

In some embodiments, the internal passages may interconnect the respective ports and a common interface aperture defined along an external surface of the implant.

In some embodiments, each of the internal passages may divide into branched paths at a respective junction. At least two of the junctions may be established between the common interface aperture and each of the respective ports.

In some embodiments, the network may be arranged according to a Fibonacci sequence such that a cross sectional area of the internal passages may progressively decrease at each of the respective junctions in a direction towards the respective ports.

In some embodiments, the implant system may include a pump securable to the common interface aperture. The pump may be configured to draw biological material from the ports at least partially into the internal passages.

In some embodiments, the common interface aperture may be defined along the plate body. The network may include a main trunk that extends outwardly from the common interface aperture. The internal passages may divide from the main trunk into branched paths coupled to the respective ports.

In some embodiments, the implant system may include a pad including a concave articulation surface. The pad may be securable to the baseplate adjacent the front face.

In some embodiments, the implant system may include an articulation head including a convex articulation surface. The articulation head may be securable to the baseplate adjacent the front face.

In some embodiments, the articulation head may include a recess dimensioned to at least partially receive the plate body.

In some embodiments, the implant may include at least one fixation aperture extending at least partially through the plate body and the augment body. The at least one fixation aperture may be configured to receive a respective fastener to secure the implant to bone.

In some embodiments, the implant may include one or more bioactive layers that establish at least a majority of surfaces of the augment body that define the network.

An orthopaedic implant system according to an exemplary aspect of the present disclosure may include an implant including a baseplate and an augment extending from the baseplate. A front face of the baseplate may be configured to face towards an opposed an articular surface associated with a bone. The augment may include an augment body including a network of internal passages coupled to respective ports along an external surface of the augment body. A pump may be configured to communicate biological material at least partially into the network.

In some embodiments, the implant may include an interface aperture defined along an external surface of the implant. The internal passages may interconnect the respective ports and the interface aperture. The pump may be securable to the implant at the interface aperture.

In some embodiments, the implant system may include an articulation member including an articulation surface that may be configured to cooperate with the opposed articular surface to establish a joint interface. The articulation member may be securable to the baseplate.

In some embodiments, the implant system may include a plurality of fasteners. The implant may include a plurality of fixation apertures. Each of the fixation apertures may be configured to receive a respective one of the fasteners to secure the implant to bone.

A method of installing an orthopaedic implant according to an exemplary aspect of the present disclosure may include positioning an implant along a surgical site. The implant may include a baseplate and an augment. The baseplate may include a plate body extending between front and rear faces. The augment may include an augment body extending from the plate body. The augment body may include a network of internal passages coupled to respective ports along an external surface of the augment body. The positioning step may occur such that the front face of the baseplate faces towards an opposed articular surface associated with an adjacent bone.

In some embodiments, the method may include coupling a pump to the network and actuating the pump to cause biological material to be communicated at least partially into the internal passages.

In some embodiments, the method may include actuating the pump in a first mode to cause at least a portion of the biological material to be drawn from surgical site, through the ports, and then at least partially into the internal passages.

In some embodiments, the method may include actuating the pump in a second mode to cause at least a portion of the biological material in the network to move outwardly in a direction towards the ports.

In some embodiments, the network may branch outwardly from the rear face of the plate body to the ports.

In some embodiments, the method may include forming a cavity in bone along the surgical site. The step of positioning the implant may include moving the augment at least partially into the cavity such that the external surface of the augment body abuts a wall of the cavity adjacent the ports.

In some embodiments, the implant may include a fixation aperture. The method may include positioning a fastener at least partially through the fixation aperture and into bone to secure the implant to the surgical site.

In some embodiments, the method may include securing an articulation member to the plate body adjacent to the front face. The articulation member may include an articulation surface that cooperates with the opposed articular surface to establish a joint interface.

In some embodiments, the surgical site may be established along a glenoid.

FIG. 1 illustrates an exemplary orthopedic implant system 20 including an implant 22 securable to a surgical site. The system 20 may be utilized for various surgical procedures, such as an arthroplasty to repair a joint. The implant 22 may be incorporated into a shoulder prosthesis, for example. Although the implants disclosed herein primarily refer to repair of a defect in a glenoid during a shoulder reconstruction, such as an anatomic or reverse shoulder procedure, it should be understood that the disclosed implants may be utilized in other locations of the patient and other surgical procedures including repair of a humerus and other joints such as a wrist, hand, hip, knee, ankle or spline, and including repair of fractures.

Figure 4:
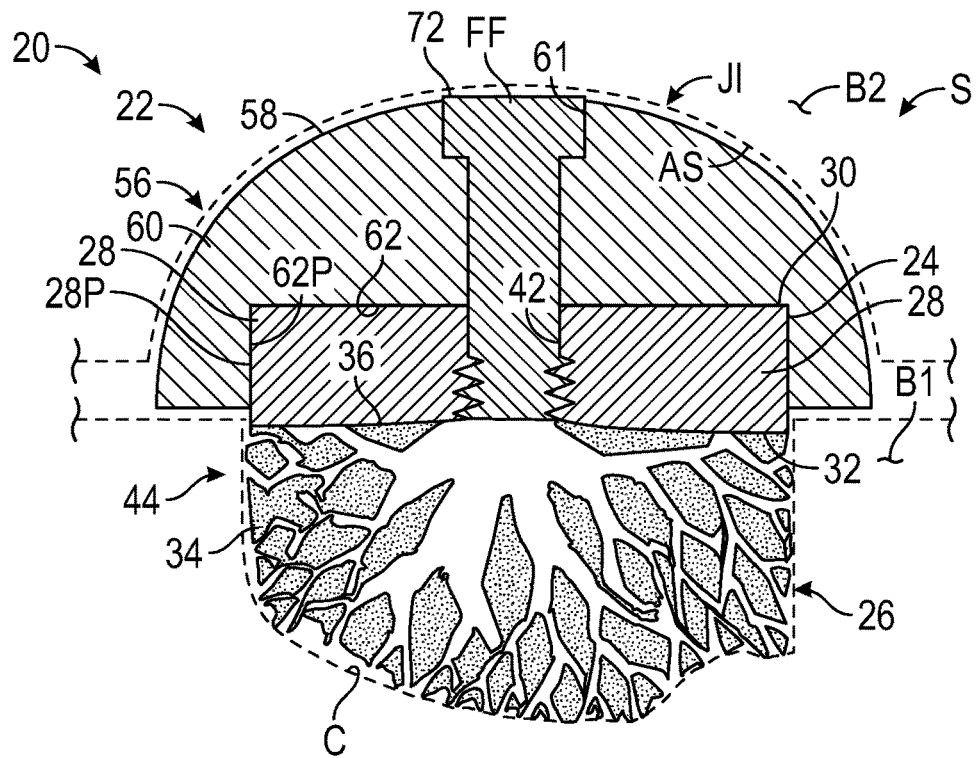
FIG. 4 illustrates a sectional view of the implant of FIG. 1 coupled to an exemplary articulation member.

The implant 22 may include a baseplate 24 and augment 26. The baseplate 24 may include a plate body 28 extending along a central axis A between a front face 30 and a rear face 32 generally opposed to the front face 30. The front face 30 may be configured to face toward an opposed articulation surface AS associated with an adjacent bone B2, as illustrated in FIG. 4. The articulation surface AS may be a portion of the bone B2 or an adjacent implant component secured to the bone B2.

The baseplate 24 may have various geometries. A perimeter of the baseplate 24 may have as a generally rectangular, elliptical, oval, oblong or complex geometry. For example, a perimeter 28P of the plate body 28 may have a substantially circular or elliptical cross-sectional geometry, as illustrated in FIG. 1. For the purposes of this disclosure, the terms "substantially" and "approximately" mean±5% of the stated relationship or value unless otherwise stated. A substantially circular geometry may reduce a reaming width and complexity of preparing a surgical site to accept the implant 22.

The augment 26 may include an augment body 34 extending between a front face 36 and a rear face 38 generally opposed to the front face 36. The augment body 34 may be disposed on and extend from the rear face 32 of the plate body 28 along the central axis A. The rear faces 32, 38 of the baseplate 24 and augment 26 may generally correspond to a medial side of a patient, and the front faces 30, 36 of the baseplate 24 and augment 26 may generally correspond to a lateral side of the patient when implanted in a surgical site, for example.

Figure 2A:
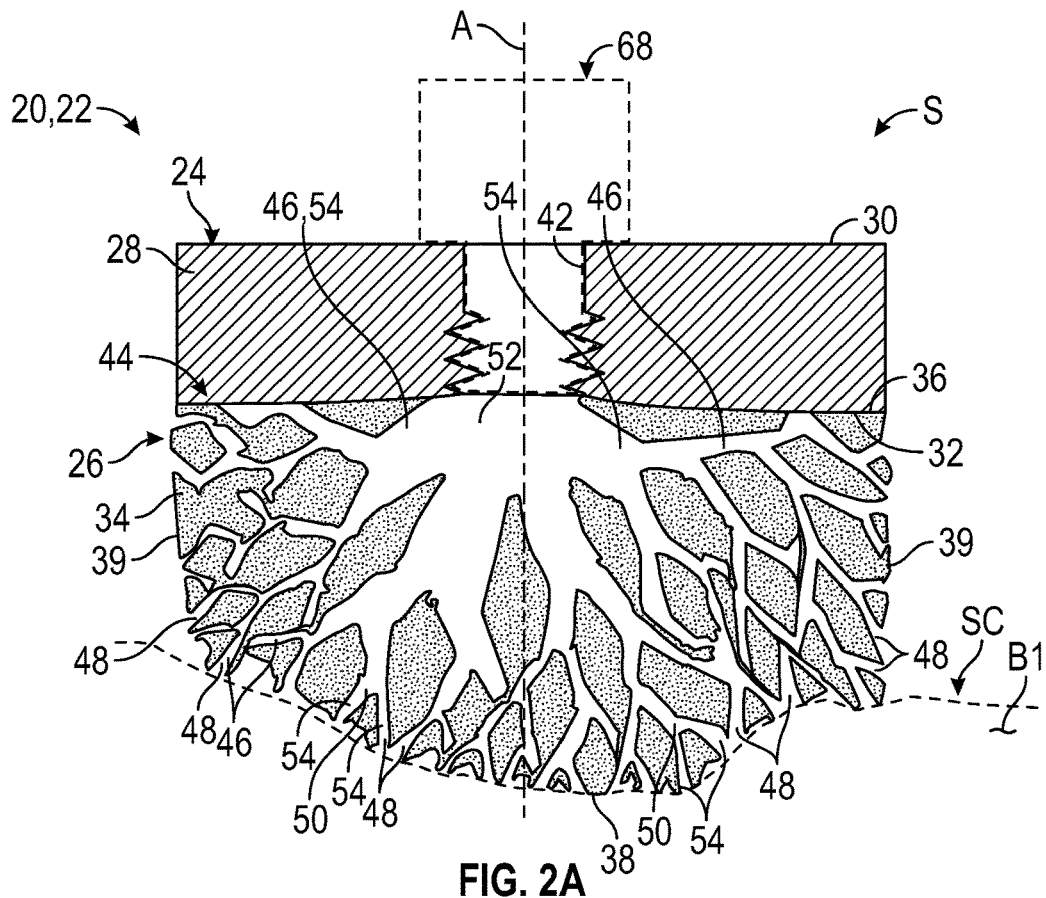
FIGS. 2A-2B illustrate sectional views of the implant taken along lines 2A-2A and 2B-2B of FIG. 1.
Figure 2B:
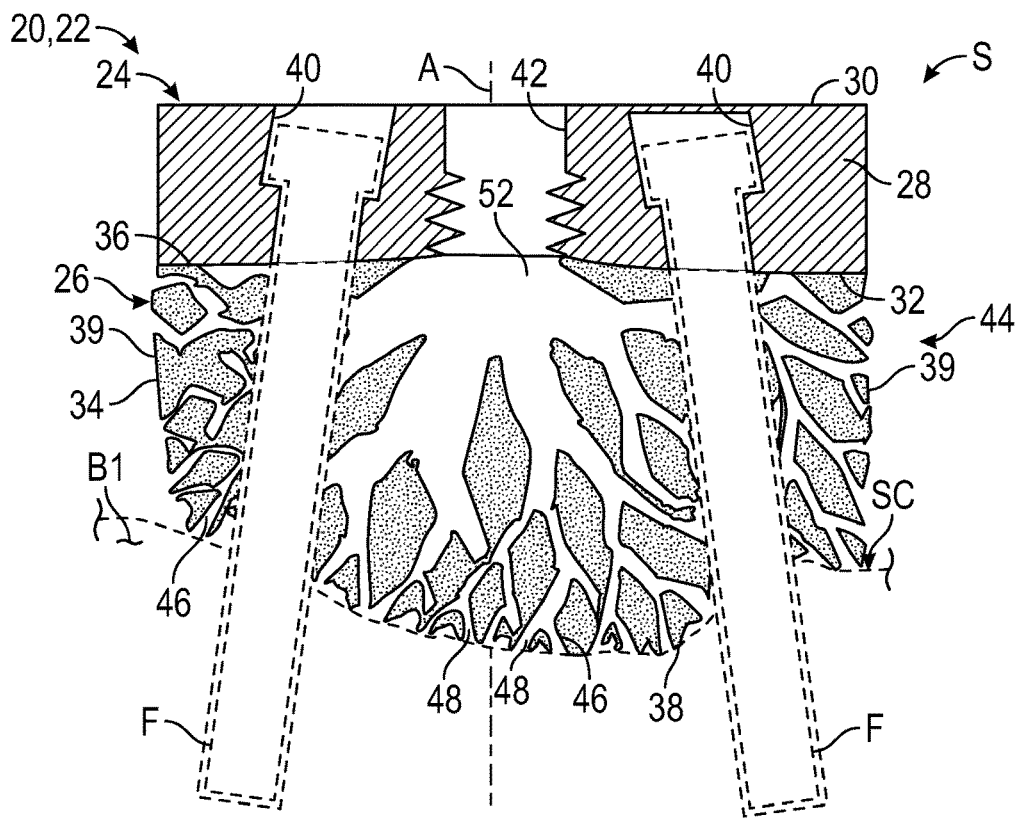

The implant 22 may include one or more fixation apertures 40. Each fixation aperture 40 may extend at least partially or completely through the plate body 28 and/or augment body 34, as illustrated in FIG. 2B. Each fixation aperture 40 may be configured to receive a respective fastener F to secure the implant 22 to tissue such as bone B1, as illustrated in FIG. 2B (B1 and F shown in dashed lines for illustrative purposes). The system 20 may include a plurality of fasteners F received in respective fixation apertures 40, as illustrated in FIG. 1. Example fasteners may include pins, nails, bolts and compression screws.

The implant 22 may include at least one interface aperture 42 defined along an external surface of the implant 22. The interface aperture 42 may extend along the central axis A between the front face 30 and rear face 32 of the plate body 28, as illustrated in FIGS. 2A-2B. The fixation apertures 40 may be distributed in an array about the interface aperture 42 and/or central axis A, as illustrated in FIG. 1. The interface aperture 42 may also serve as a fixation aperture. The interface aperture 42 may be established along another portion of the implant 22. For example, the interface aperture may be established along an external surface of the augment body, as illustrated by interface aperture 242 of FIG. 6. The interface aperture 242 may be established along a sidewall 239 of the augment body 234 at a position between a front face 236 and a rear face 238 of the augment body 234. In this disclosure, like reference numerals designate like elements where appropriate and reference numerals with the addition of one-hundred or multiples thereof designate modified elements that are understood to incorporate the same features and benefits of the corresponding original elements.

Referring to FIG. 2A, with continuing reference to FIG. 1, the augment 26 may be dimensioned to approximate various defect geometries and surface contours that may be encountered along a surgical site S. In some implementations, a geometry of the augment 26 may be patient-specific based on one or more measurements of an anatomy of the patient. The rear face 38 of the augment 26 may be dimensioned to contact tissue such as bone B1 along the surgical site S. The rear face 38 may be dimensioned to overlay a surface contour SC along the bone B1, as illustrated in FIG. 2A-2B. In other implementations, the augment 26 may be inlaid in the bone B1 to at least partially or completely fill a volume of a cavity C in the bone B1, and the baseplate 24 may be at least partially received in the cavity C, as illustrated in FIG. 4.

The augment body 34 may include an internal network 44 for conveying blood, nutrients, bone marrow and other biological material to promote intraosseous integration of the implant 22 and healing of the patient. The biological material may be provided by the patient or from another source. The internal network 44 may be utilized to communicate other materials in the implant 22, including non-biological materials. Example non-biological materials may include a cement material to improve fixation, and antibiotics such as gentamicin to reduce the risk of infection at the bone-implant interface along the surgical site S, for example.

The internal network 44 may be defined at least partially or completely within a thickness of the augment body 34 between the front face 36 and rear face 38. The internal network 44 may have a predefined geometry dimensioned to establish a network of internal passages 46 coupled to respective ports 48 along the external surface of the augment body 34. For purposes of this disclosure, the term "predefined" means an engineered construct that excludes random arrangements such as meshes and porous materials.

The internal passages 46 may be dimensioned to establish respective flow paths between the interface aperture 42 and one or more of the respective ports 48. The internal passages 46 may be dimensioned to interconnect the interface aperture 42 and respective ports 48 along the external surface of the augment 26. One or more of the internal passages 46 may branch to the respective ports 48.

The interface aperture 42 may be common to each of the internal passages 46 and ports 48, as illustrated in FIGS. 2A-2B. In other examples, the implant 22 may include more than one interface aperture 42, each coupled to a respective set of internal passages 46. The network 44 may be dimensioned to branch outwardly from the rear face 32 of the plate body 28 and/or front face 36 of the augment body 34 to the ports 48 along opposed sidewalls 39 and/or rear face 38 of the augment body 34, as illustrated in FIGS. 2A-2B. The sidewalls 39 may have a substantially smooth and continuous profile to facilitate positioning of the augment 26 in the cavity C (FIG. 4).

The interface aperture 42 may be defined along the plate body 28. The network 44 may include a main trunk 52 that extends outwardly from the interface aperture 42. The network 44 may be established such that one or more (or each) of the internal passages 46 is dimensioned to divide from the main trunk 52 into branched paths 54 coupled to respective ports 48. The internal passage 46 may divide into the branched paths 54 at a respective junction 50. At least two junctions 50 may be established between the interface aperture 42 and each of the respective ports 48, such that at least some of the internal passages 46 are branched paths 54 divided from another internal passage 46. The arrangement of internal passages 46 may reduce localized stress concentrations in the augment 26.

Figure 3:
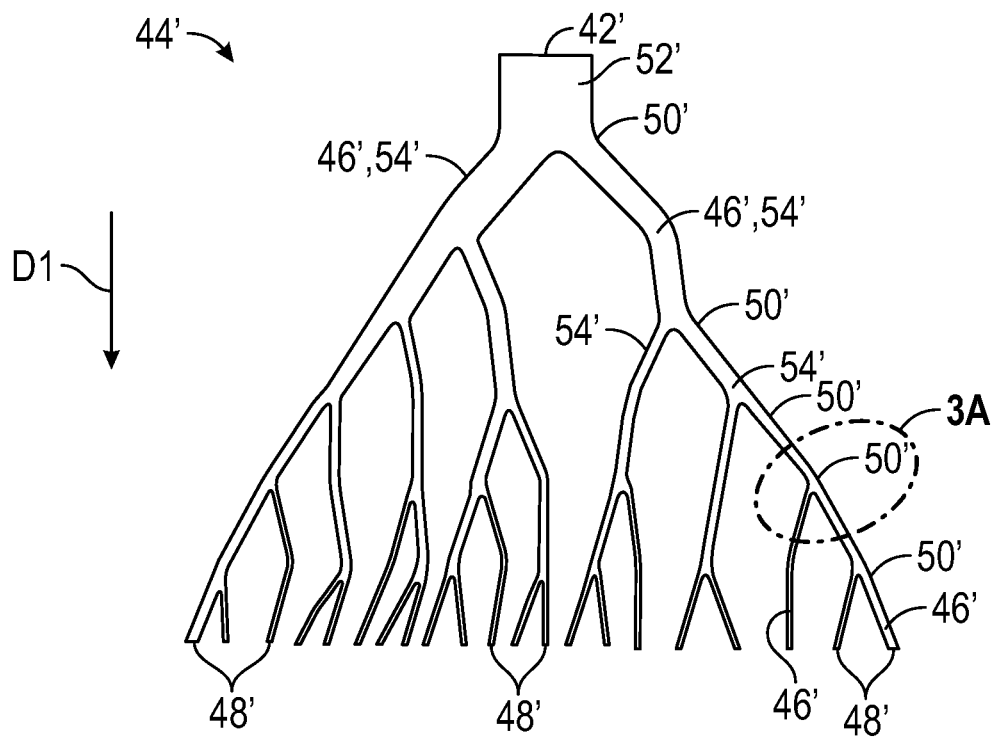
FIGS. 3-3A illustrate an example network of internal passages.
Figure 3A:
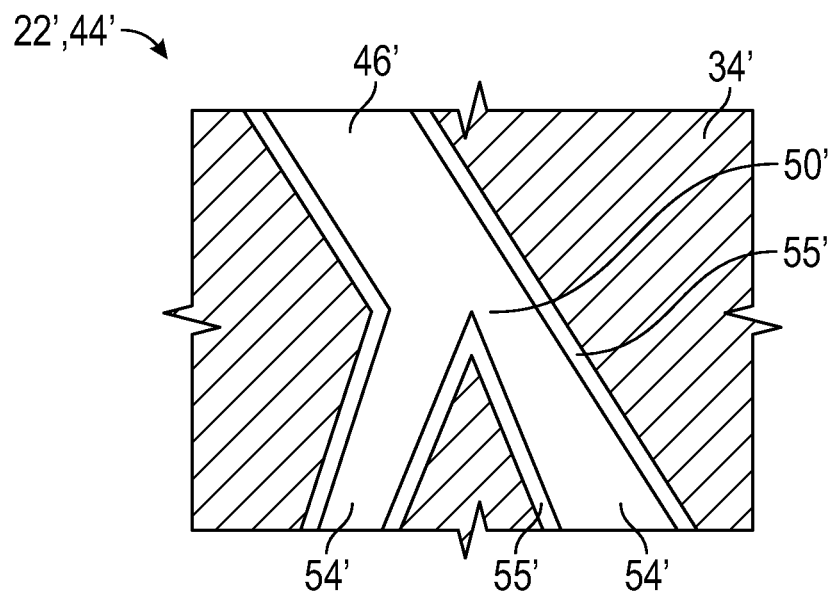

In the illustrative example of FIG. 3, network 44' includes at least three junctions 50' established between an interface aperture 42' and a respective one of the ports '48. The internal passage 46' may divide into at least two branched paths 54' at a respective junction 50', as illustrated in FIG. 3A. A cross-sectional area of each internal passage 46' in the network 44' may be equal to or greater than a combined cross-sectional area of the branched paths 54' that divide from the internal passage 46' at the respective junction 50'. For example, the internal passage 46' of FIG. 3A may have a cross-sectional area of approximately 8 mm, and the two branched paths 54' may each have a cross-sectional area of approximately 4 mm at the junction 50' to yield a total cross-sectional area of approximately 8 mm. The cross-sectional area of the main trunk 52' may be equal to or greater than a summation of the cross-sectional areas of all of the downstream junctions 50' in the network 44'. The cross-sectional areas of the junctions 50' may decrease sequentially from the main trunk 52' in a direction D1. For example, the network 44' may be predefined according to a Fibonacci sequence such that a cross-sectional area of each internal passages 46' progressively decreases in a series of the respective junctions 50' in the direction D1 from interface aperture 42' toward the respective ports 48', although an opposite arrangement may be utilized.

The internal passages 46 including the branched paths 54 may be established in various orientations to communicate material throughout the internal network 44 including between the interface aperture 42 and ports 48. In implementations, the internal network 44 may be dimensioned to generally mimic nature such as a root system of a tree. Portions of internal passages 46 may branch outwardly from the interface aperture 42 such that the portions of the internal passages 46 are radially offset from each other relative to the longitudinal axis A of the implant 22. Portions of the internal passage 46 may be established on opposed sides of an adjacent portion of the internal passage 46, as illustrated by branched paths 54 of the respective internal passages 46. Projections of the branched paths 54 may intersect each other on a common plane, as illustrated by FIG. 2A, but may be radially offset from each other by a thickness of the augment body 34, as illustrated by FIG. 2B taken along line 2B-2B of FIG. 1. The branched paths 54 may be coupled to respective ports 48 at different circumferential positions relative to the longitudinal axis A (see, e.g., FIG. 1).

Referring to FIG. 4, the implant system 20 may include an articulation member 56 securable to the baseplate 24 adjacent the front face 30. The articulation member 56 may have an articulation surface 58. The articulation surface 58 may be configured to cooperate with the opposed articulation surface AS to establish a joint interface JI.

The articulation member 56 may have various geometries that complement the articulation surface AS. For example, the articulation member 56 may be an articulation head 60 having a generally convex articulation surface 58, as illustrated in FIG. 4. The articulation head 60 may be a glenosphere secured to a glenoid in a reverse shoulder repair procedure, for example.

The articulation member may have other geometries. As illustrated by implant 122 of FIG. 5, articulation member 156 includes a pad 164 having an articulation surface 158. The articulation surface 158 may have a generally concave geometry. The articulation member 156 may be utilized in a anatomic shoulder repair procedure, for example. The pad 164 may be securable to a baseplate 124 adjacent a front face 130. At least one peg 166 may extend outwardly from a body of the pad 164. The peg 166 may be dimensioned to be secured in a hole H1 in the bone B1 to provide fixation along the surgical site S. The pad 164 may include at least one protrusion 167 that is dimensioned to mate with the interface aperture 142 to limit relative movement between the baseplate 124 and pad 164.

Figure 5:
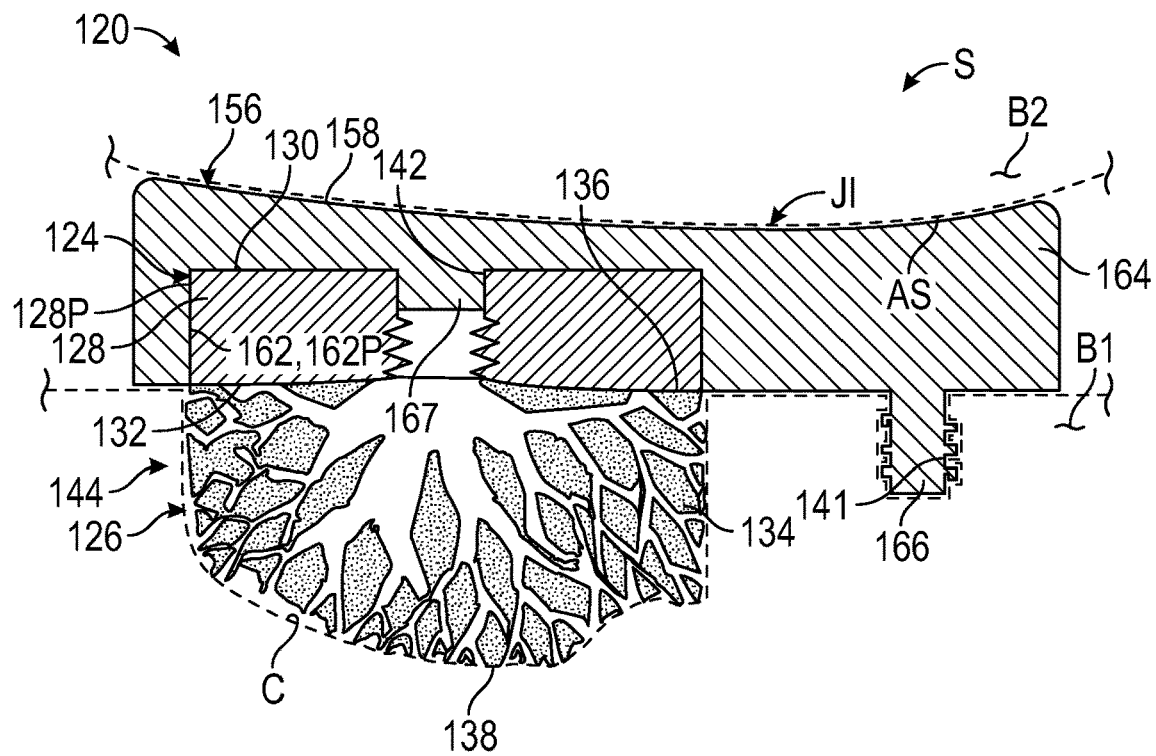
FIG. 5 illustrates another sectional view of the implant of FIG. 1 coupled to an exemplary articulation member.

Various techniques may be utilized to secure the articulation members 56, 156 to the respective baseplates 22, 122. The articulation members 56, 156 may be mechanically attached or releasably secured to the respective baseplate 24, 124. Referring to FIGS. 4 and 5, the articulation members 56, 156 may include a respective recess 62, 162 dimensioned to at least partially receive the respective plate body 28, 128. However, an opposite configuration can be utilized. A perimeter 62P/162P of the recess 62/162 may be dimensioned to encircle a perimeter 28P/128P of the plate body 28/128 adjacent the front face 30/130. The perimeter 28P/128P of the plate body 28/128 may be dimensioned to cooperate with the perimeter 62P/162P of the recess 62/162 to establish a Morse taper connection to secure the articulation member 56/156 to the baseplate 24/124. The articulation member 56/156 may be impacted or pressed on the baseplate 24/124 to establish an interference fit or otherwise seat the articulation member 56/156. The articulation head 60 may include an aperture 61 dimensioned to receive a respective fastener FP. The fastener FP may be at least partially received in the interface aperture 42 and cooperate with threading to mechanically attach the articulation head 60 to the baseplate 24 and assist in alignment of the articulation head 60.

The articulation members 56, 156 may be provided together in a kit to the surgeon. The kit may include articulation members 56, 156 having different shapes and/or sizes for selection by the surgeon based on an anatomy of the patient.

Figure 6:
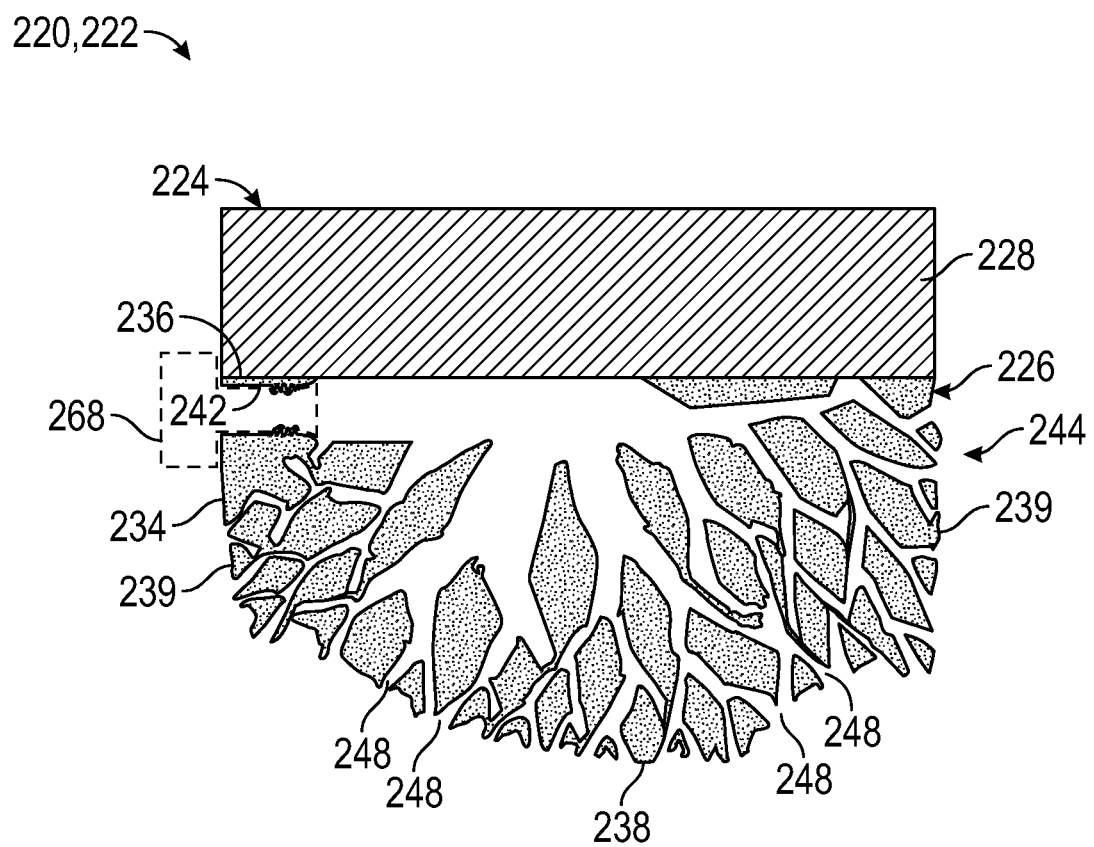
FIG. 6 illustrates a sectional view of another exemplary implant system.

Referring back to FIG. 2A, the implant system 20 may include a pump 68 selectively coupled to the implant 22 (shown in dashed lines for illustrative purposes, see also implant 222 of FIG. 6). The pump 68 may be securable to the interface aperture 42 via a threaded connection, for example. The pump 68 may be configured to convey material through at least a portion of the internal network 44 in operation (see, e.g., pump 368 of FIG. 12). The pump 68 may be configured to draw or otherwise communicate blood, bone marrow and other tissue, nutrients, other biological material and/or other material from the patient adjacent the surgical site S and at least partially into the internal network 44 to promote intraosseous integration of the implant 22 and healing of the patient, including any of the materials disclosed herein. In implementations, the pump 68 may be configured to convey or deliver biological material from an external supply to the network 44, such as biological material from the patient or a donor gathered prior to placement of the implant 22.

Various techniques may be utilized to form the implant 22. The implant 22 may be a monolithic arrangement in which the baseplate 24 and augment 26 may be integrally formed, or the implant 22 may be a modular arrangement that may include separate components that are mechanically attached or otherwise secured to each other. The augment 26 may be printed or otherwise formed on the baseplate 24 according to a predefined geometry to establish a three-dimensional scaffold. The scaffold establishes the internal network 44, which extends at least partially through a volume of the augment 26.

Various materials may be utilized to form the components of the implant systems disclosed herein. The disclosed baseplates, augments and articulation members may be made of surgical grade metallic materials. Example metallic materials include titanium alloys such as Ti6A14V and cobalt-based materials such as cobalt-chromium (CoCr). Non-metallic materials may be utilized, such as an ultra-high-molecular-weight polyethylene (UHMWPE). The pad 164 (FIG. 5) may be made of a non-metallic material, including any of the non-metallic materials disclosed herein. Portions of the implant such as the augment may be constructed from a biological and other bio-materials, such hydroxyapatite and allograft bone or other tissue.

The plate body of the baseplate may comprise a first material, and the augment body of the augment may comprise a second material. The first and second materials may be same or can differ in composition and/or construction. For example, a density of the first and second materials can be same or can differ. The plate body may be substantially solid.

One or more coatings or layers may be deposited along surfaces of the implant, including the baseplate and/or augment. For example, at least one layer 55' may be disposed along or otherwise establish surfaces of the augment body 34', as illustrated in FIG. 3A. The implant 22' may include one or more layers(s) 55' that establish at least a majority or substantially all surfaces of the augment body 34' that define the network 44'. The layer(s) 55' may include any of the materials disclosed herein, including a non-biological material or a bioactive material or biologics that promote intraosseous integration of the implant 22' at the surgical site. Example layers may include calcium phosphate (CaP) and hydroxyapatite for promoting bone growth. The layer(s) 55' may be disposed on surfaces of the implant 22' concurrently or subsequent to formation of the implant 22'. For example, the layer(s) 55' may be printed to establish surfaces of the internal network 44' while printing adjacent portions of the implant 22'. In other implementations, the layer(s) 55' may be deposited on surfaces of the augment body 34 to establish surfaces of the network 44'. For example, the layer(s) 55' may be injected as a slurry into the network 44' subsequent to formation of the implant 22'.

Figure 7:
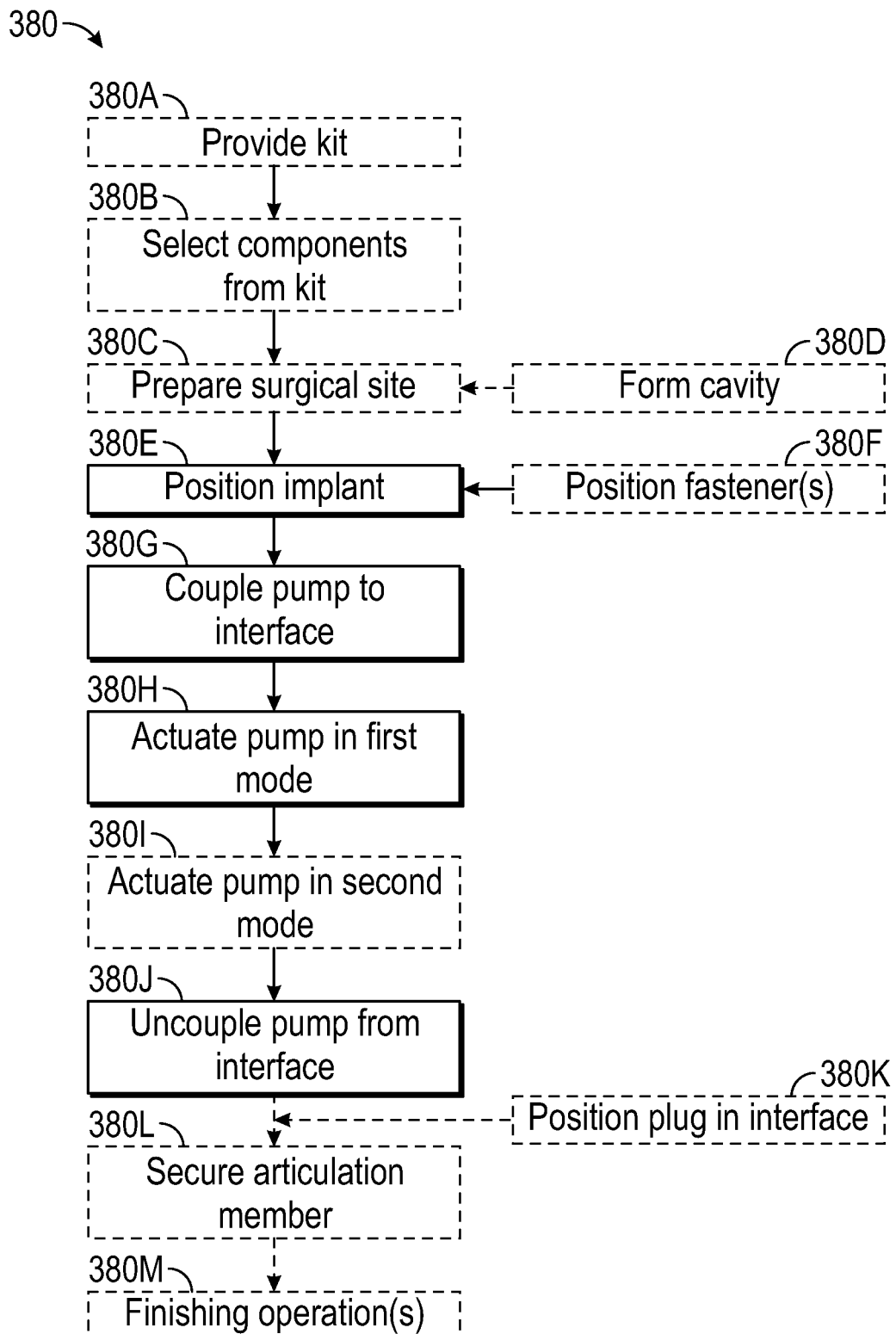
FIG. 7 illustrates an exemplary method of installing an orthopaedic implant.

FIG. 7 illustrates an exemplary method of installing an orthopaedic implant at a surgical site in a flowchart 380. The method may be utilized to perform an arthroplasty for restoring functionality to shoulders and other joints having advanced cartilage disease, such as repairing bone defects along a glenoid, for example. Although the method 380 primarily refers to implants for repair of a defect in a glenoid during a shoulder reconstruction, it should be understood that the method and disclosed implants may be utilized in other locations of the patient and other surgical procedures, such as the humerus or any other location disclosed herein. The method 380 can be utilized with any of the orthopedic implant systems disclosed herein. Fewer or additional steps than are recited below could be performed within the scope of this disclosure, and the recited order of steps is not intended to limit this disclosure.

Figure 8:
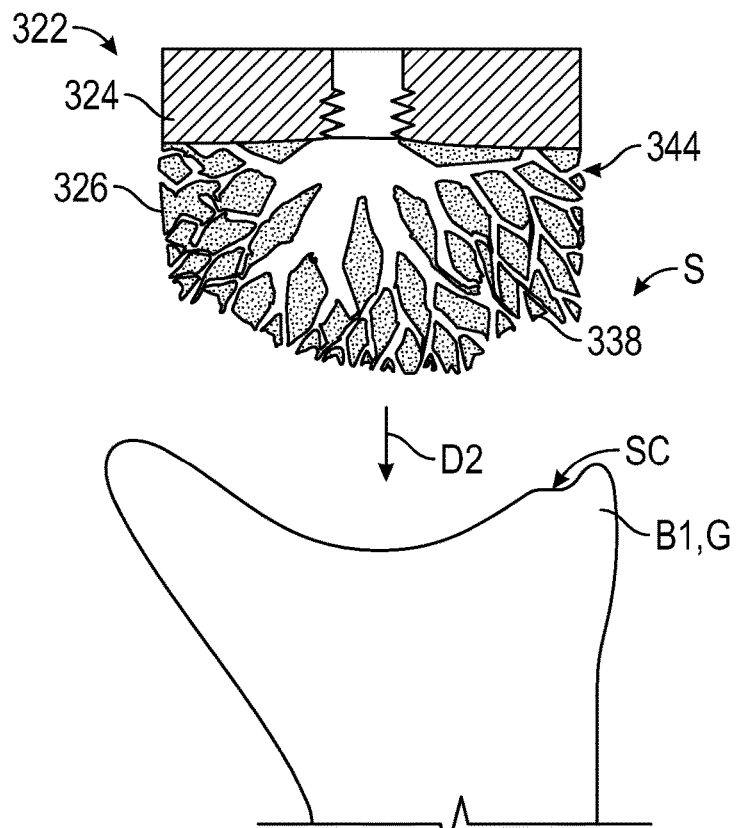
FIGS. 8-9, 9A and 10-13 illustrates an exemplary implant system in various modes, positions and states relative to a surgical site.

A kit for arthroplasty may be provided at step 380A. The kit may include any of the components of the implant systems disclosed herein. The kit may include a set of implants of various sizes and geometries. At step 380B the surgeon may select one or more components from the kit. For example, step 380B may include selecting an implant from a set of implants based on the planned surgical technique and/or an anatomy of the patient including a surface contour SC associated with a bone B1 along a surgical site S, as illustrated in FIG. 8. The surgical site S may be established along a glenoid G, for example. The kit may include fasteners of different sizes that may be received in respective apertures in the implant to secure the implant to the surgical site S. The kit may include articulation members of various sizes and geometries for securing to a selected implant. The surgeon may select an articulation member from the kit based on the planned surgical technique and/or the anatomy of the patient.

Referring to FIG. 8, with continuing reference to FIG. 7, the surgical site S can be prepared for receiving an implant 322 at step 380C. The implant 322 may correspond to any of the implants disclosed herein. The implant 322 can include a baseplate 324 and augment 326. One or more operations may be performed to prepare the surgical site S, such as one or more reaming, milling and/or drilling operations to establish a specified geometry of the surgical site S. Step 380C may include forming one or more holes in the surgical site dimensioned to receive respective fasteners (see, e.g., FIG. 2B).

Figure 10:
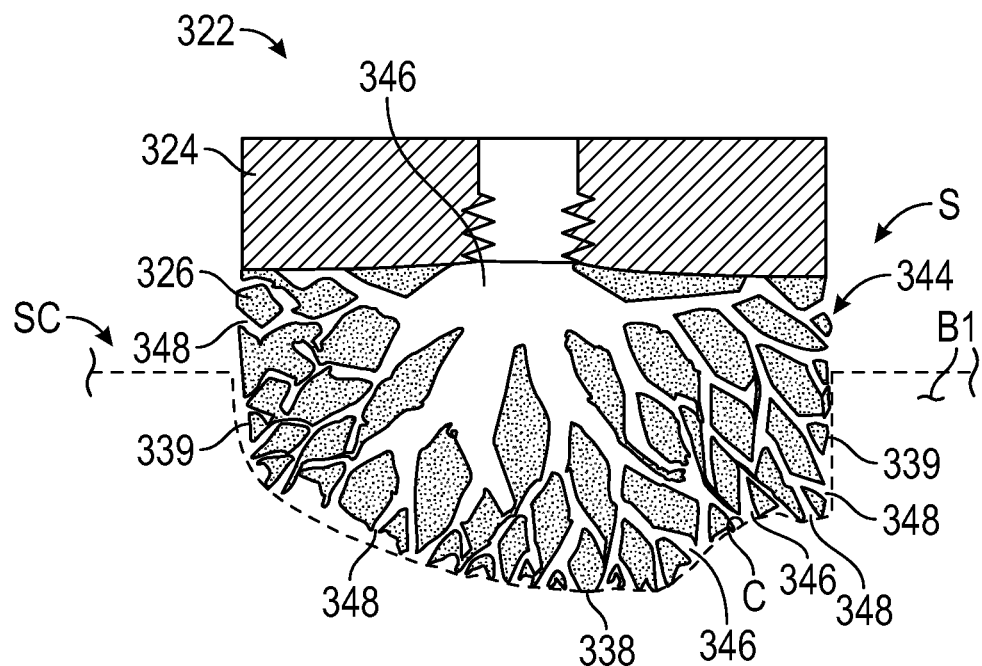
Figure 11:
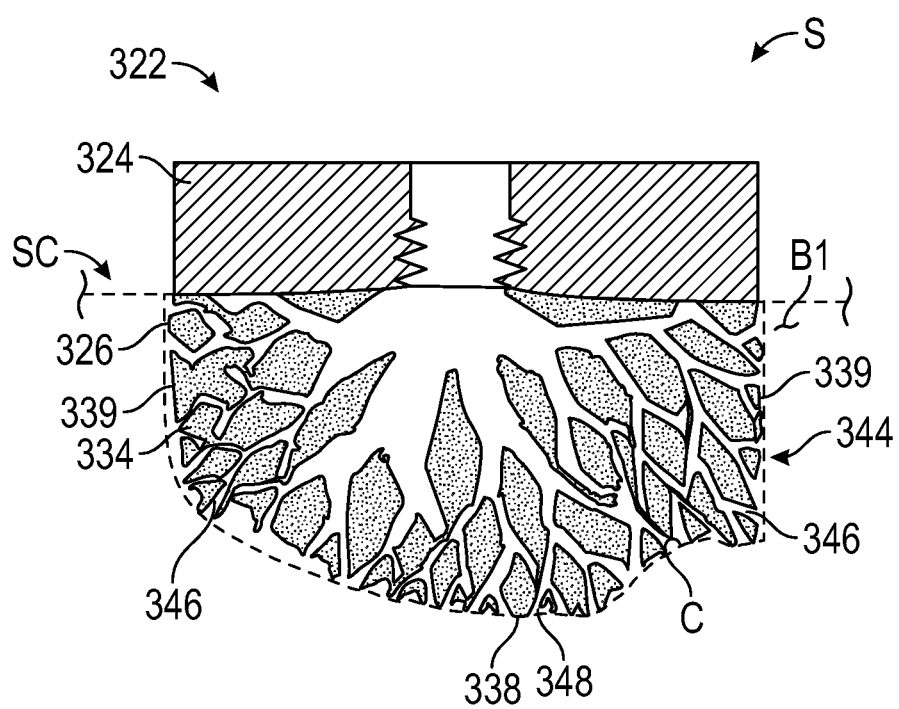

Step 380C may include forming a cavity C along the surgical site S, such as an articulating surface of the glenoid G, at step 380D. The cavity C may be formed by removing a portion of the bone B1 or other tissue at the surgical site S, as illustrated in FIGS. 10 and 11. The tissue may include cartilage, cancellous bone and/or cortical bone along the surgical site S.

The cavity C may be dimensioned to at least partially or completely receive the baseplate 324 and/or augment 326. The cavity C may be formed to remove tissue from a defect in the bone B1 and may be dimensioned to approximate a profile of the defect. A defect in the glenoid can be characterized by the Walch Classification. The surgeon may measure bone loss utilizing imaging of the surgical site, such a radiogram or computed tomography technique, or may approximate a profile of the defect utilizing one or more sizers and/or measuring devices placed against the bone surface.

Figure 13:
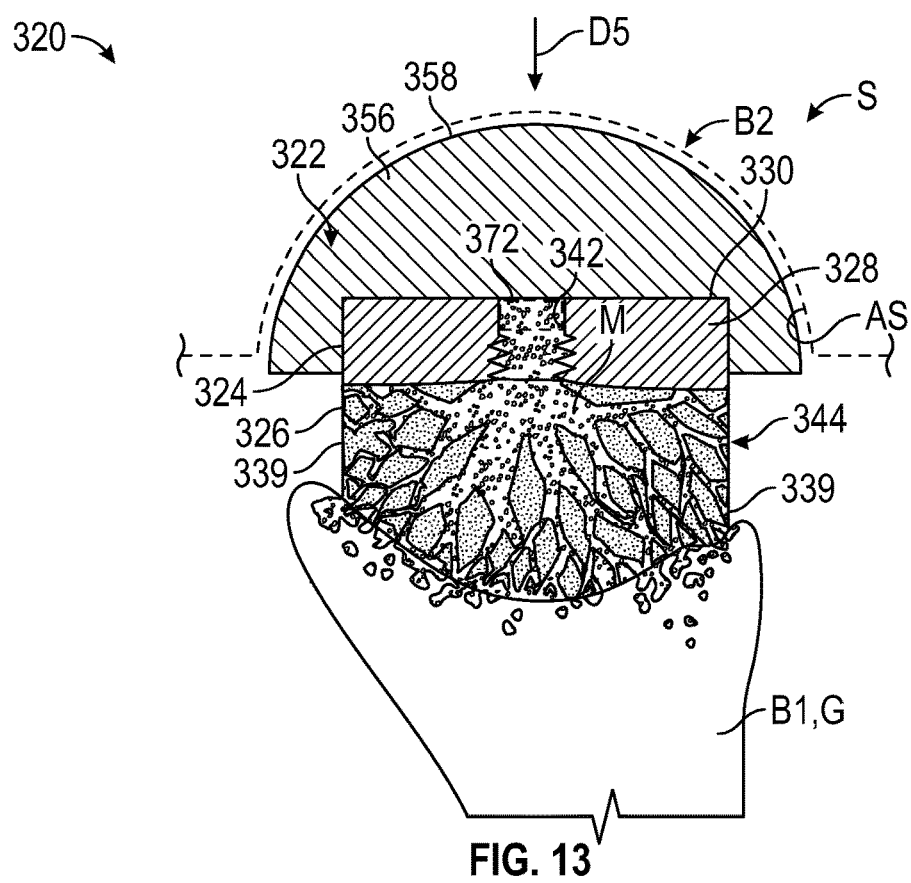

The selected implant 322 may be positioned along the surgical site S at step 380E. Step 380E may occur such that the front face 330 of the baseplate 324 faces towards an opposed articular surface AS associated with an adjacent bone B2, as illustrated in FIG. 13.

Figure 9:
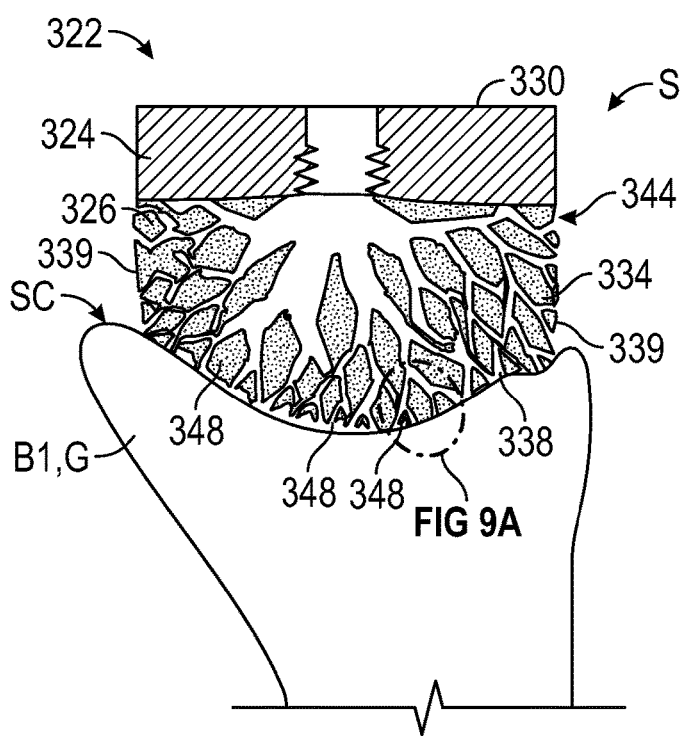

Referring to FIGS. 8 and 9, with continuing reference to FIG. 7, step 380E may include moving the implant 322 in a direction D2 (FIG. 8) such that the rear face 338 abuts against and overlays the surface contour SC of the bone B1, as illustrated in FIG. 9. In some implementations, the implant 322 is positioned such that at least the augment 326 abuts a surface and/or fills the cavity C along the surgical site S. For example, step 380E may include positioning the augment 326 partially in the cavity C, as illustrated in FIG. 10, or positioning the augment 326 completely in the cavity C as illustrated in FIG. 11. Step 380E may include positioning at least a portion of the baseplate in the cavity, as illustrated by the baseplate 24 of FIG. 4.

Step 380E may include moving the augment 326 at least partially into the cavity C such that an external surface of the augment body 334 abuts a wall of the cavity C adjacent the ports 348, as illustrated in FIGS. 10-11. External walls of the augment body 334 may have a substantially smooth or continuous contour, including sidewalls 339. One or more ports 348 may be defined in the sidewalls 339 to promote communication of biological material M subsequent to placement of the implant 322 and completion of the surgical procedure.

Figure 9A:
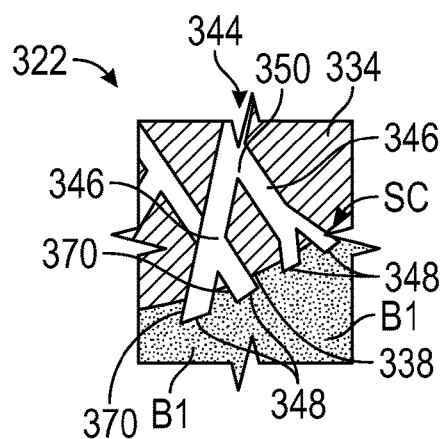

In some implementations, the augment body 334 may include one or more protrusions 370 extending outwardly from the rear face 338 or another portion of the augment body 334, as illustrated in FIG. 9A. The protrusions 370 may be dimensioned to resemble one or more roots extending outwardly from the rear face 338. Each protrusion 370 may define at least one of the internal passages 346 and ports 348. Step 380E may include moving the implant 322 into abutment with a surface of the bone B1 such that the protrusions 370 are at least partially embedded in the bone B1, which may improve fixation of the implant 322 along the surgical site S.

At step 380F, one or more fasteners may be positioned in and at least partially through a respective fastener aperture, and then into bone to secure the selected implant to the surgical site, as illustrated by the fasteners F of FIG. 2B. The fasteners F may be compression screws that can serve to apply and maintain compression between the baseplate 24 and bone surface which may reduce relative motion and tissue formation that may otherwise occur due to spacing between the contact surfaces of the implant and bone.

Abutment of the augment 326 against the adjacent bone B1 may establish a wicking or capillary action. The wicking action may cause biological material M from the surgical site S to at least partially or completely fill a volume of the internal network 344, which can promote bone growth and fixation of the implant 322.

Figure 12:
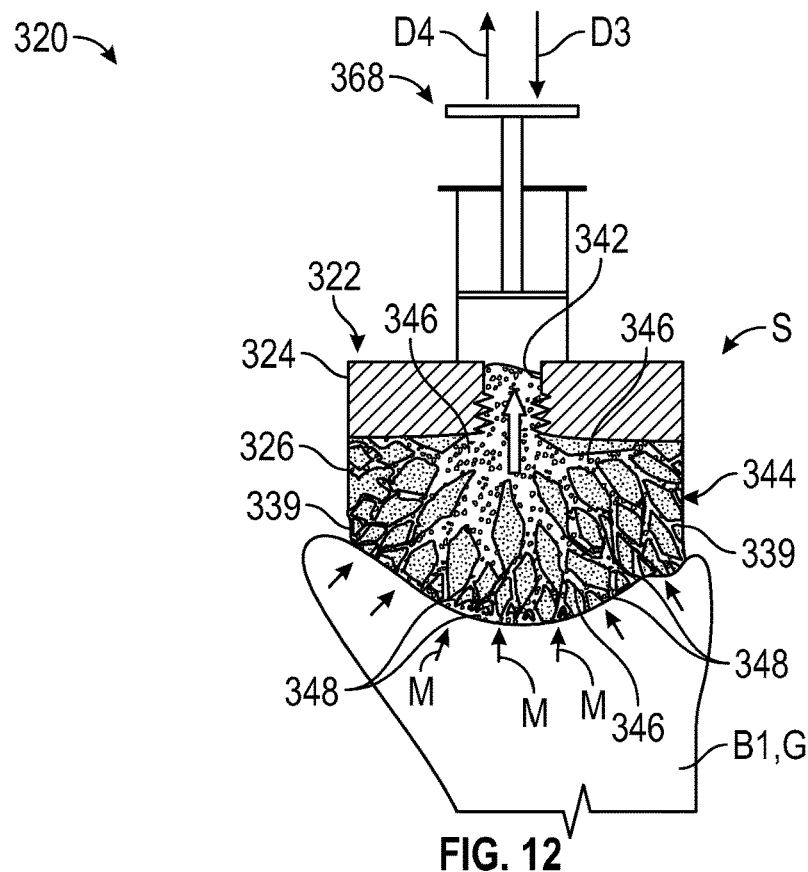

Referring to FIG. 12, with continuing reference to FIG. 7, in some implementations a pump 368 may be coupled to an internal network 344 of the implant 322 at step 380G. The pump 368 may include one or more modes. For example, the pump 368 may be a bi-directional pump such as a syringe movable in a third direction D3 during a first mode and moveable in a fourth direction D4 during a second mode. The fourth direction D4 may be generally opposed to the third direction D3. The pump 368 may serve to draw biological material into the internal network 344 and/or move the biological material M toward the interface aperture 342 in the first mode. The pump 368 may serve to move biological material M away from the interface aperture 342 and through the internal network 344 in the second mode.

At step 380H, the pump 368 may be actuated to cause biological and/or other material M to be communicated at least partially into the internal passages 346 of the internal network 344. Step 380H may include actuating the pump 368 in one or more modes, such as the first mode and/or second mode. At step 380H, the pump 368 may be actuated in the first mode to cause at least a portion of the biological material M to be drawn from the surgical site S, through the ports 348, and then at least partially into the internal passages 346 such that a volume of the internal network 344 is at least partially or substantially filled with the biological material M. At step 380I, the pump 368 may be actuated in the second mode to cause at least a portion of the biological material M in the network 344 to be pushed or otherwise move outwardly in a direction towards the ports 348. In some implementations, step 380I may include conveying non-biological material and/or biological material M from the pump 368 to the internal network 344, which may be provided by the patient or from another source. The pump 368 may be actuated in one or more cycles between the first and second modes to at least partially or substantially fill a volume of the internal network 344 with the non-biological material and/or biological material M. The pump 368 may be uncoupled from the interface aperture 342 of the implant 322 at step 380J.

The interface aperture 342 may be utilized to obtain a visual indication of an amount of the biological material M that is contained in the internal network 344. The surgeon may repeat steps 380G, 380H, 380I and/or 380J until a determined portion of the internal network 344 is filled with the biological material M.

Referring to FIG. 13, with continuing reference to FIG. 7, a plug 372 may be positioned in the interface aperture 342 to at least partially seal the internal network 344 at step 380K (shown in dashed lines for illustrative purposes). The plug 372 may be made of any of the materials disclosed herein. In other implementations, the plug 372 is omitted. In some implementations, the fastener FF of FIG. 4 may serve as a plug 72.

An articulation member 356 may be secured to the baseplate 324 at step 380L. The articulation member 356 can include any of the articulation members disclosed herein. The articulation member 356 may be moved in a direction D5 and brought into abutment with the baseplate 324. The articulation member 356 may be secured to the plate body 328 adjacent to the front face 330. An articulation surface 358 of the articulation member 356 may be arranged to mate with an opposed articular surface AS. The articulation surface AS may be established by an adjacent bone B2 or by another implant situated along the adjacent bone B2. The adjacent bone B2 may be a humerus that opposes the glenoid G, for example.

One or more subsequent and/or finishing operations may be performed at step 380M. Example finishing operations may include closing an incision adjacent the surgical site S.

The novel implants and methods of this disclosure can provide improved fixation and healing of the patient. The disclosed implants may include augments internal networks that receive biological material, which can improve intraosseous integration and fixation of the implant through the promotion of bone growth into the internal network. The disclosed internal networks including interconnected branches and nodes may emulate the structural, junctional and/or physiological properties of the native bone and improve force distribution to encourage structural adaption of the adjacent bone, which may improve fixation of the implant.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A method of installing an orthopaedic implant comprising:
    positioning an implant along a surgical site;
    wherein the implant includes a baseplate, an augment and a fixation aperture, the baseplate includes a plate body extending between front and rear faces, the augment includes an augment body extending from the plate body, the fixation aperture includes a first section that extends through the plate body and a second section that extends through the augment body, the augment body includes a network of internal passages coupled to respective ports along an external surface of the augment body, and the positioning step occurs such that the front face of the baseplate faces towards an opposed articular surface associated with an adjacent bone;
    wherein the plate body includes a common interface aperture, the internal passages interconnect the respective ports and the common interface aperture, the network includes a main trunk extending outwardly from the common interface aperture, and each of the internal passages divides from the main trunk into branched paths at a respective junction such that at least two of the junctions are established between the common interface aperture and each of the respective ports; and
    positioning a fastener at least partially through the first and second sections of the fixation aperture and into bone to secure the implant to the surgical site.

2. The method as recited in claim 1, further comprising:
    coupling a pump to the network; and
    actuating the pump to cause biological material to be communicated at least partially into the internal passages.

3. The method as recited in claim 2, further comprising:
    actuating the pump in a first mode to cause at least a portion of the biological material to be drawn from the surgical site, through the ports, and then at least partially into the internal passages.

4. The method as recited in claim 3, further comprising:
    actuating the pump in a second mode to cause at least a portion of the biological material in the network to move outwardly in a direction towards the ports.

5. The method as recited in claim 2, further comprising:
actuating the pump in a second mode to cause at least a portion of the biological material in the network to move outwardly in a direction towards the ports.

6. The method as recited in claim 2, wherein the coupling step includes securing the pump to the common interface aperture at the front face of the plate body.

7. The method as recited in claim 6, further comprising:
actuating the pump in a first mode and/or a second mode;
wherein actuating the pump in the first mode causes at least a portion of the biological material to be drawn from the surgical site, through the ports, and then at least partially into the internal passages; and
wherein actuating the pump in the second mode causes at least a portion of the biological material in the network to move outwardly in a direction towards the ports.

8. The method as recited in claim 7, wherein the step of the actuating the pump includes actuating the pump in the first mode and actuating the pump in the second mode.

9. The method as recited in claim 7, further comprising:
sealing the common interface aperture subsequent to the step of the actuating the pump in the first mode.

10. The method as recited in claim 7, wherein the network is arranged according to a Fibonacci sequence such that a cross sectional area of the internal passages progressively decreases at each of the respective junctions in a direction towards the respective ports.

11. The method as recited in claim 1, wherein the network branches outwardly from the rear face of the plate body to the ports.

12. The method as recited in claim 1, further comprising:
forming a cavity in the bone along the surgical site; and
wherein the step of positioning the implant includes moving the augment at least partially into the cavity such that the external surface of the augment body abuts a wall of the cavity adjacent the ports.

13. The method as recited in claim 1, further comprising:
securing an articulation member to the plate body adjacent to the front face; and
wherein the articulation member includes an articulation surface that cooperates with the opposed articular surface to establish a joint interface.

14. The method as recited in claim 1, wherein the surgical site is established along a glenoid.

15. The method as recited in claim 1, wherein:
the main trunk extends outwardly from the common interface aperture at the rear face of the plate body;
the internal passages extend from the main trunk in a direction away from the rear face of the plate body towards the external surface of the augment body; and
the network is arranged according to a Fibonacci sequence such that a cross sectional area of the internal passages progressively decreases at each of the respective junctions in a direction from the main trunk towards the respective ports.

* * * * *